United States Patent [19]
Freitas

[11] Patent Number: 5,224,951
[45] Date of Patent: Jul. 6, 1993

[54] SURGICAL TROCAR AND SPIKE ASSEMBLY

[75] Inventor: Michael Freitas, Irving, Tex.

[73] Assignee: Dexide, Inc., Fort Worth

[21] Appl. No.: 675,985

[22] Filed: Feb. 19, 1991

[51] Int. Cl.$^5$ .............................................. A61B 17/32
[52] U.S. Cl. .................... 606/172; 606/185; 128/754
[58] Field of Search ............... 604/164, 165, 166–169, 604/272–274, 22, 51; 606/167–172; 128/751–754

[56] References Cited
U.S. PATENT DOCUMENTS 4,654,030 3/1987 Moll et al. ......................... 604/165
4,869,717 9/1989 Adair ................................... 604/51

Primary Examiner—C. Fred Rosenbaum
Assistant Examiner—Manuel Mendez
Attorney, Agent, or Firm—Jackson & Walker

[57] ABSTRACT

A surgical trocar instrument is provided which includes a trocar spike designed to prevent coring of the needlepoint of a trocar tube and which is secured to a knob or holding assembly in a manner that the trocar tube resists relative rotational movement and the spike assembly is biased outwardly of the needlenose of the trocar tube, but the bias may be overcome upon insertion of the trocar tube through a cavity wall, with the bias moving the spike assembly outwardly of the trocar tube to prevent coring during additional surgical maneuvers.

23 Claims, 2 Drawing Sheets

SURGICAL TROCAR AND SPIKE ASSEMBLY

BACKGROUND OF THE INVENTION (1) Field of the Invention

This invention is related to surgical trocar instruments.

(2) Brief Description of the Prior Art

Trocars are sharp-pointed instruments used to puncture a body cavity. Such puncturing is often necessary so that fluids may be drained to or from a body using a cannula which is inserted into the opening. Trocars are also used during endoscopic surgical procedures which basically follow three steps. First, a Veress or other cannula is inserted into the abdominal cavity through the abdominal wall and the cavity is inflated with insufflating gas which is passed through the cannula. After insufflating, a small incision is made in the skin and a trocar spike is thrust into the inflated abdomen through the bore of the trocar tube. Standard trocar "spikes" are shaped like a large metal peg with a sharpened needlenose point at the end. The spike is inserted for purposes of puncturing or cutting of the abdominal wall and piercing the fascia and peritoneum inside the cavity. Thereafter, the trocar spike is removed and an endoscopic surgical instrument is inserted into the abdominal cavity through the trocar tube.

A serious problem associated with conventional and prior art trocar "spikes" is that such devices which are hollow and cylindrically shaped can puncture internal organs and arteries, and also may receive the solids which are cut or punctured within the body cavity to cause same to be contained and housed within the outboard-most end of the trocar spike, resulting in a "coring" effect similar to that experienced when a cylindrical cutting device is inserted through an apple. Such "coring" is undesirable for many obvious reasons, including the fact that a buildup of such solid material interior of the trocar tubular spike can cause trauma, bleeding and damage to organs and arteries, and can further complicate surgical procedures.

The present invention is directed to overcoming the problems associated with prior art trocar spikes.

SUMMARY OF THE INVENTION

The surgical trocar instrument comprises an elongate trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an outboard open end extendable through said second opposite open end of said trocar housing and an inboard end, said cylindrical housing defining, preferably, an elliptical configuration terminating in a sharp needlepoint at the outboard-most end of said cylindrical housing. Coring prevention means are received within the cylindrical housing and are biased for extension outboard of said tip for urging the solid material interior of the cavity away from the needlepoint and the open end of the cylindrical housing while the cylindrical housing is moved through the solid material interior of the cavity. In a preferred embodiment, means, such as a spring assembly, are provided for applying a concentric bias between the cylindrical housing and the coring prevention means.

In the preferred embodiment, locking means are provided around the inboard end of the cylindrical housing for hand positioning of the cylindrical housing through the trocar housing with locking means defined on the coring prevention means and the means defined around the inboard end of the cylindrical housing, for locking interengagement therebetween.

In the preferred embodiment, the coring prevention means includes a plow-shaped end extending through the open end of the cylindrical housing, the configuration of such end providing the separation of tissue without trauma or hematoma.

DESCRIPTION OF THE PREFERRED EMBODIMENTS

Figure 1:
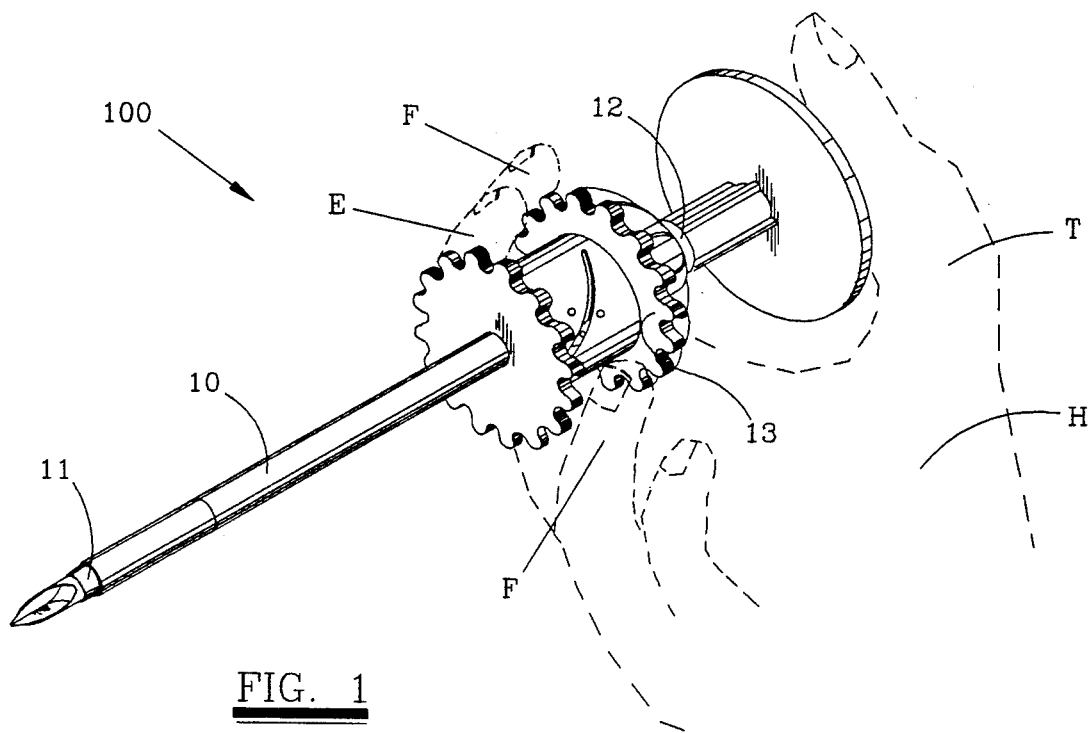
FIG. 1 is an isometric view of the surgical trocar and spike assembly of the present invention in hand-held position.

Now, with first reference to FIG. 1, there is shown the surgical trocar instrument 100 of the present invention held between three fingers F and the thumb T on the hand H of an operator. As shown, the instrument shown 100 has an elongate trocar tubular housing 10 with a front open end 11 at its outboardmost end and a second opposite open end 12 inboard thereof. A holder 13 is disposed around the tubular housing 10 for convenient holding of the instrument 100 during surgical operations.

Figure 3:
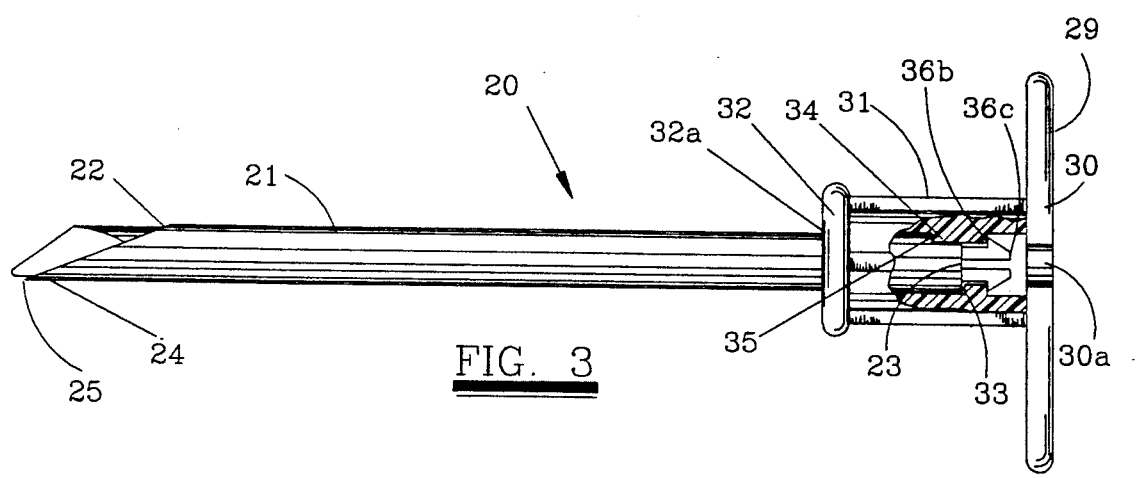
FIG. 3 is a horizontal elongate partial exterior partial interior view of the trocar and spike assembly of the present invention and the locking interrelationship between the core prevention means and the cylindrical housing interior of a knob or member.
Figure 4:
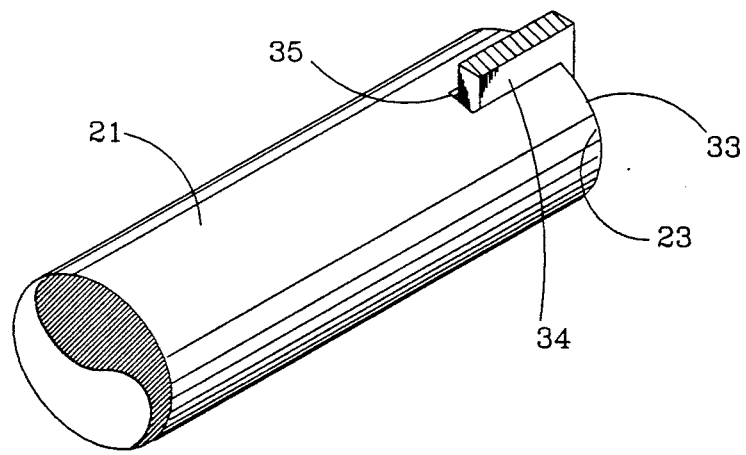
FIG. 4 is an interior view of the locking interrelationship between core prevention means and the cylindrical housing.

Now with reference to FIGS. 1 and 3, the elongate trocar spike assembly 20 of the present invention is shown inserted interior of the trocar tubular housing 10 (FIG. 1). The spike assembly 20 is shown prior to insertion in or subsequent to removal from the trocar housing 10 in FIG. 3. The spike assembly 20 includes a cylindrical housing 21 having an outboard open end 22 and an inboard open end 23 positioned within a knob assembly 29. The outboard open end 22 is elliptically configured as shown by line 24 terminating in a needlepoint 25.

Figure 2:
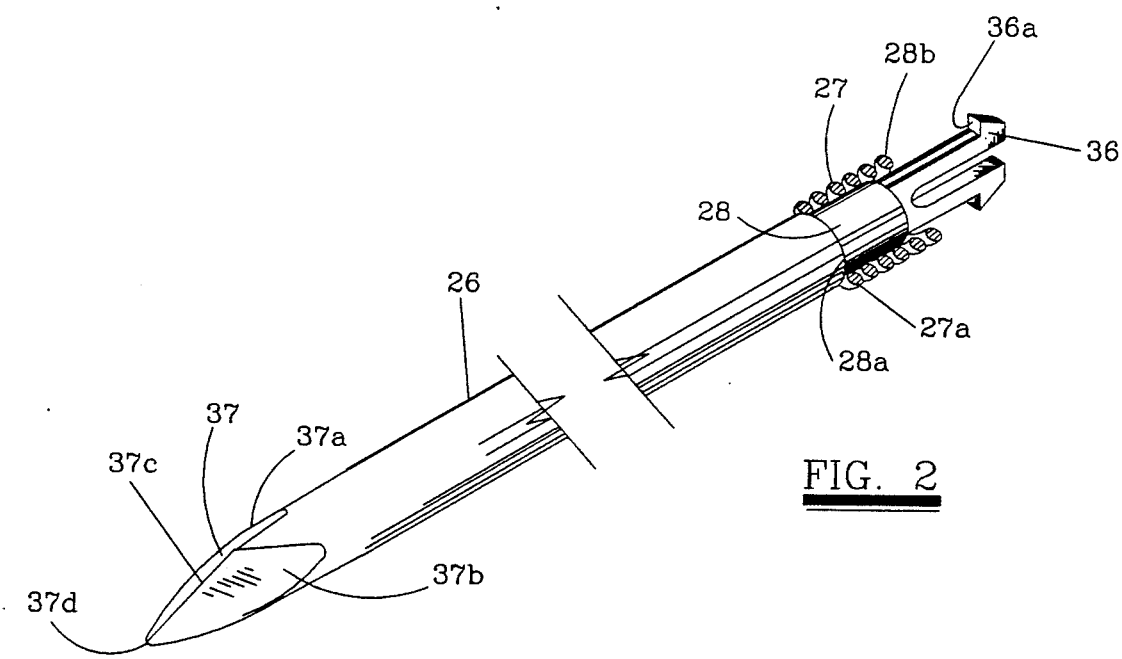
FIG. 2 is an exterior elongated view of the coring prevention means of the trocar spike assembly.

With reference to FIG. 2, the coring prevention means 26 is carried within the cylindrical housing 21 of the spike assembly 20. A means for applying a bias between the coring prevention means 26 and the cylindrical housing 21 is provided by means, such as a spring 27, carried around a spring groove 28 on the core prevention means 26. The outermost end 27a of the spring 27 snuggly rests against an abutting outwardly protruding shoulder 28a on the coring prevention means 26, with the inner end 28b of the spring 27 snuggly engaging a spring shoulder 33 in the knob assembly 29 (FIG. 3).

The coring prevention means 26 has at its inboardmost end a locking means which is shown preferably as a series of flexible collet fingers 36 having a snap shoulder 36a which is secured against a companion shoulder 36b in the knob assembly 29 and on the knob central housing 31 thereof. As the coring prevention means 26 is inserted within the cylindrical housing 21 through the outboard open end 22, the collet fingers 36 will be permitted to flex inwardly within the cylindrical housing. 21, but will flex outwardly upon passage through the knob central housing 31 subsequent to the snap shoulder 36a passing inwardly, slightly, of the securing shoulder 36b. Accordingly, the collet fingers 36 will "snap" into place, such that the interengagement between the securing shoulder 36b and the snap shoulder 36a prevent further outboard movement of the coring prevention means 26 relative to the cylindrical housing 21.

The coring prevention means 26 is contourly shaped at its outboard-most end to provide a plow-shaped end 37 consisting of contoured face members 37a, 37b terminating in a blunt nose 37d, with a rib 37c separating the faces 37a, 37b.

As shown in FIG. 3, the knob assembly 29 consists of a knob 30 for urging of the trocar spike assembly 20 into the tubular housing 10 by application of an operator's thumb T onto the knob 30, as in FIG. 1.

The knob assembly 29 has extending from the knob 30 a central housing 31 which, in turn, terminates in a round knob frontal housing 32 having a central opening 32a for insertion of the cylindrical housing 21 therethrough. A rib 34 is defined interiorly on the central housing 31 for companion receipt within a profiled slot 35 on the cylindrical housing 21 such that interrelationship between the rib 34 and the slot 35 prevents relative rotational movement between the cylindrical housing 21 and the knob assembly 29.

A central bore 30a is defined through the knob 30 for receipt of the tip end 36c of the collet fingers 36 indicating retraction of the end 37 as the needlepoint 25 of the cylindrical housing 21 surgically cuts into a member within the cavity housing.

ASSEMBLY AND OPERATION

The elongate trocar spike assembly 20 of the present invention may be used in any conventional tubular trocar, such as the surgical trocar instrument 100 and housing 10 shown in FIG. 1. Those skilled in the art will appreciate that the spike assembly 20 of the present invention will find utility and application in any one of a number of conventional trocar tubular housings 10.

In assembly, the coring prevention means 26 with the spring 27 positioned as shown in FIG. 2 is inserted through the outboard open end 22 of the spike assembly 20 with the knob assembly 29 being securely placed around the inboard open end 23 of the housing 21. As the coring prevention means 26 is introduced through the cylindrical housing 21, the collet fingers 36 will flex radially inwardly around the smooth interior wall of the cylindrical housing 21 until the snap shoulder 36a of the finger 36 passes slightly past the securing shoulder 36b. At such time, the collet fingers 36 will flex outwardly such that the coring prevention means 26 is locked into the cylindrical housing 21 and cannot be removed therefrom. As shown in FIG. 3, the tip 36b of the coring prevention means 26 is interior of the bore 30a, indicating that the nose 37d and the plow-shaped end 37 of the coring prevention means 26 is in alignment with the needlepoint 25 of the cylindrical housing 21. Now, the spike assembly 20, may be thrust through the second opposite open end 12 of the elongate trocar tubular housing 10 by application of the operator's thumb T (or in the base of the hand H) onto the knob 30 and by holding the holder 13 in the fingers F as shown in FIG. 1.

As the needlepoint 25 of the cylindrical housing 21 contacts the body within the cavity through which surgical cutting is to be performed, the bias afforded by the engagement of the spring 27 between the shoulder 28a on the coring prevention means 26 and the shoulder 33 on the knob central housing 31 will be overcome, and the plow-shaped end 37 will move inwardly, such that the nose 37d is inboard, just slightly, of the needlepoint 25 of the cylindrical housing 21. However, because of the plow-shaped configuration of the end 37 on the coring prevention means 26, solid matter cut at the needlepoint 25 will not be permitted to enter interior of the cylindrical housing 21 and will be pushed away from the needlepoint 25 as surgical cutting is continued.

When it is desired to terminate the cutting procedure, the spike assembly 20 is manipulated by hand out of the trocar tubular housing 10, and the spring 27 will bias the coring prevention means 26 outwardly relative to the cylindrical housing 21, thus further assuring that all solid matter interior of the body cavity is moved away from the needlepoint 25 by means of the plow-shaped end 37, thus eliminating the "coring" effect, described above.

It will be appreciated that as the nose 37d of the coring prevention means 26 moves away, slightly, from the needlepoint end 25 of the cylindrical housing 21, the tip 36c of the collet finger assembly 36 will pass interior of the bore 30a and exterior, just slightly, of the knob 30, thus indicating to the operator that the coring prevention means 26 is in such position during operating procedure.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A surgical trocar instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining an elliptical configuration terminating in a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall, and means for applying a concentric bias between said cylindrical housing and said coring prevention means, wherein said coring prevention means includes a plow-shaped end extending through said open end of said cylindrical housing.

2. The instrument of claim 1 further including means for securing said cylindrical housing relative to said coring prevention means.

3. The instrument of claim 1 further including means positioned around the inboard end of said cylindrical housing for hand positioning of said cylindrical housing through said trocar housing.

4. The instrument of claim 3: said means defined around the inboard end further including means for engagement with said cylindrical housing to prevent relative rotational movement between said cylindrical housing and said coring prevention means.

5. The instrument of claim 3 further including locking means defined on said coring prevention means and said means defined around the inboard end of said cylindrical housing, for locking interengagement therebetween.

6. The instrument of claim 5 wherein said locking means comprises a series of flexible collet fingers defined around said coring prevention means for receipt interior of said means positioned around the inboard end of said cylindrical housing.

7. The instrument of claim 5 wherein one of said coring prevention means and said means positioned around the inboard end of said cylindrical housing defines a series of flexible collet fingers for locking engagement relative to a companion locking surface defined on the other end of said coring prevention means and said means positioned around the inboard end of said cylindrical housing.

8. A surgical trocar instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall; and means for applying a concentric bias between said cylindrical housing and said coring prevention means, wherein said coring prevention means includes a plow-shaped end extending through said open end of said cylindrical housing.

9. A surgical trocar instrument, comprising: an elongated trocar housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall, wherein said coring prevention means includes a plow-shaped end extending through said open end of said cylindrical housing.

10. A surgical instrument introducible through a trocar, said trocar having an elongate tubular housing having a first open end portion for positioning through a body wall and a second open end portion for introduction and removal of auxiliary surgical therethrough while said first open end portion is positioned through the body wall, said surgical instrument comprising: an elongated trocar tubular housing having a first open end portion for positioning through a body wall and a second opposite open end for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining an elliptical configuration terminating in a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall; and means for applying a concentric bias between said cylindrical housing and said coring prevention means, wherein said coring prevention means includes a plow-shaped end extending through said open end of said cylindrical housing.

11. The instrument of claim 1 or 10, the bias on said coring prevention means being overcome to move said coring prevention means inwardly relative to said cylindrical housing and away from said needle point by introduction of said cylindrical housing through said body wall, said bias moving said coring prevention means toward said needle point and positioning said coring prevention means outboard of said needle point subsequent to introduction through said body wall.

12. The surgical instrument of claim 10 further including means for securing said cylindrical housing relative to said coring prevention means.

13. The surgical instrument of claim 10 further including means positioned around the inboard end of said cylindrical housing for hand positioning of said cylindrical housing through said trocar housing.

14. The surgical instrument of claim 13: said means defined around the inboard end further including means for engagement with said cylindrical housing to prevent relative rotational movement between said cylindrical housing and said coring prevention means.

15. The surgical instrument of claim 13 further including locking means defined on said coring prevention means and said means defined around the inboard end of said cylindrical housing, for locking interengagement therebetween.

16. The surgical instrument of claim 15 wherein said locking means comprises a series of flexible fingers defined around said coring prevention means for receipt interior of said means positioned around the inboard end of said cylindrical housing.

17. The surgical instrument of claim 15 wherein one of said coring prevention means and said means positioned around the inboard end of said cylindrical housing defines a series of flexible collet fingers for locking engagement relative to a companion locking surface defined on the other end of said coring prevention means and said means positioned around the inboard end of said cylindrical housing.

18. The surgical instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall; and means for applying a concentric bias between said cylindrical housing and said coring prevention means, wherein said coring prevention means includes a plow-shaped end extending through said open end of said cylindrical housing.

19. A surgical instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing an inboard end and an outboard open end extendable through said second opposite open end of said trocar housing, said cylindrical housing defining a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall, wherein said coring prevention means includes a plow-shaped end extending through said open end of said cylindrical housing.

20. A surgical trocar instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining an elliptical configuration terminating in a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall and means for applying a concentric bias between said cylindrical housing and said coring prevention means, the bias on said coring prevention means being overcome to move said coring prevention means inwardly relative to said cylindrical housing and away from said needle point by introduction of said cylindrical housing through said body wall said bias moving said coring prevention means toward said needle point and positioning said coring prevention means outboard of said needle point subsequent to introduction through said body wall, and further including means positioned around the inboard end of said cylindrical housing for hand positioning of said cylindrical housing through said trocar housing, including locking means defined on said coring prevention means and said means defined around the inboard end of said cylindrical housing, for locking interengagement therebetween, said means positionable around the inboard end defining a bore therethrough for receipt of indicating end members of said locking means when the bias on said coring prevention means is overcome and said coring prevention means is moved inwardly relative to said cylindrical housing.

21. A surgical trocar instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining a sharp needle point at the outboard-most end of said cylindrical housing; and coring prevention means received within said cylindrical housing and biased for extension outboard of said needle point for urging solid material interior of said body wall away from said needle point and said open end of said cylindrical housing while said cylindrical ,housing is moved through said solid material interior of said body wall; and means for applying a concentric bias between said cylindrical housing and said coring prevention means, the bias on said coring prevention means being overcome to move said coring prevention means inwardly relative to said cylindrical housing and away from said needle point by introduction of said cylindrical housing through said body wall, said bias moving said coring prevention means toward said needle point and positioning said coring prevention means outboard of said needle point subsequent to introduction through said body wall, and further including means positioned around the inboard end of said cylindrical housing for hand positioning of said cylindrical housing through said trocar housing, including locking means defined on said coring prevention means and said means defined around the inboard end of said cylindrical housing, for locking interengagement therebetween, said means positionable around the inboard end defining a bore therethrough for receipt of indicating end members of said locking means when the bias on said coring prevention means is overcome and said coring prevention means is moved inwardly relative to said cylindrical housing.

22. A surgical trocar instrument, comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining a sharp needle point at the outboard-most end of said cylindrical housing; and coring prevention means received within said cylindrical housing and biased for extension, outboard of said needle point for urging solid material interior of said body wall away from said needle point and said open end of said cylindrical housing while said cylindrical housing is moved through said solid material interior of said body wall, the bias on said coring prevention means being overcome to move said coring prevention means inwardly relative to said cylindrical housing and away from said tip by introduction of said cylindrical housing through said body wall, said bias moving said coring prevention means toward said needle point and positioning said coring prevention means outboard of said needle point subsequent to introduction through said body wall, and further including means positioned around the inboard end of said cylindrical housing for hand positioning of said cylindrical housing through said trocar housing, including locking means defined on said coring prevention means and said means defined around the inboard end of said cylindrical housing, for locking interengagement therebetween, said means positionable around the inboard end defining a bore therethrough for receipt of indicating end members of said locking means when the bias on said coring prevention means is overcome and said coring prevention means is moved inwardly relative to said cylindrical housing.

23. A surgical instrument introducible through a trocar, said trocar having an elongate tubular housing having a first open end portion for positioning through a body wall and a second open end portion for introduction and removal of auxiliary surgical devices therethrough while said first open end portion is positioned through the body wall, said surgical instrument comprising: an elongated trocar tubular housing having a first open end portion for positioning through a body wall and a second opposite open end portion for introduction and removal of auxiliary surgical devices therethrough while said first open end portion is positioned through the body wall; an elongate trocar spike assembly concentrically insertable through said second open end and comprising a cylindrical housing including an inboard end and an outboard open end extendable through said second opposite open end of said trocar housing, said cylindrical housing defining an elliptical configuration terminating in a sharp needlepoint at the outboard-most end of said cylindrical housing; and coring prevention means received within said cylindrical housing and biased for extension outboard of said needle point for urging solid material interior of said body wall away from said needle point and said open end of said cylindrical housing while said cylindrical housing is moved through said solid material interior of said body wall; and means for applying a concentric bias between said cylindrical housing and said coring prevention means, the bias on said coring prevention means being overcome to move said coring prevention means inwardly relative to said cylindrical housing and away from said needle point by introduction of said cylindrical housing through said body wall, said bias moving said coring prevention means toward said needle point and positioning said coring prevention means outboard of said, needle point subsequent to introduction through said body wall, and further including means positioned around the inboard end of said cylindrical housing for hand positioning of said cylindrical housing through said trocar housing, including locking means defined on said coring prevention means and said means defined around the inboard end of said cylindrical housing, for locking interengagement therebetween, said means positionable around the inboard end defining a bore therethrough for receipt of indicating end members of said locking means when the bias on said coring prevention means is overcome and said coring prevention means is moved inwardly relative to said cylindrical housing.

* * * * *